United States Patent [19]
Woolhouse et al.

[11] Patent Number: 5,397,547
[45] Date of Patent: Mar. 14, 1995

[54] METHOD OF STERILIZING THE HOSE OF A HOSE PUMP

[75] Inventors: Fred Woolhouse, Beckenham/Kent, Great Britain; Ulrich Rotermund, Oelde; Josef Bönhoff, Wadersloh, both of Germany

[73] Assignee: Westfalia Separator AG, Oelde, Germany

[21] Appl. No.: 146,298

[22] Filed: Nov. 2, 1993

[30] Foreign Application Priority Data

Dec. 11, 1992 [DE] Germany .................. 42 41 760.0

[51] Int. Cl.⁶ .................................................. A61L 2/06
[52] U.S. Cl. .......................................... 422/38; 422/26; 422/33
[58] Field of Search ................ 422/1, 25, 26, 28, 33, 422/38, 292, 295, 297, 300, 307, 294; 206/349, 379, 382

[56] References Cited

U.S. PATENT DOCUMENTS

| | | | |
|---|---|---|---|
| 338,334 | 8/1888 | Bartlett et al. | 206/379 |
| 3,630,647 | 12/1971 | Kochlin | 417/474 |
| 4,162,004 | 7/1979 | Thomas | 206/349 |
| 4,340,139 | 7/1982 | Wilcox et al. | 206/349 |
| 4,353,367 | 10/1982 | Hunter et al. | 422/300 |
| 4,721,123 | 1/1988 | Cosentino et al. | 134/57 R |
| 4,783,321 | 11/1988 | Spence | 422/300 |
| 5,078,266 | 1/1992 | Rackley | 206/349 |

Primary Examiner—Robert J. Warden
Assistant Examiner—T. A. Trembley
Attorney, Agent, or Firm—Sprung Horn Kramer & Woods

[57] ABSTRACT

A method of and device for sterilizing the hose of a hose pump in a system operating in sterile conditions. Before the system is sterilized, the hose is transferred from the pump, but not disconnected from the system's lines, to a device that surrounds it snugly. The device comprises two halves. Each half has a depression shaped and dimensioned to match half the outer surface of the hose and accordingly surrounding it tightly over its total length when the two halves are together.

9 Claims, 3 Drawing Sheets

5,397,547

METHOD OF STERILIZING THE HOSE OF A HOSE PUMP

BACKGROUND OF THE INVENTION

The present invention concerns a method of and device for sterilizing the hose of a hose pump in a system operating in sterile conditions.

Hose pumps are particularly appropriate for forwarding and regulating the flow of aggressive materials and for the sterile and gentle forwarding of sensitive materials. The material is forwarded through a line by a roller or shoe revolving on the circumference of a wheel and squeezing the hose at a point that advances downstream. The material downstream of the squeeze is accordingly conveyed from the suction end to the compression end. The hose returns to its original shape when the roller lifts off it, generating a vacuum that helps forward the material. The hose must of course be resilient.

Pumps that forward sterile materials are employed in systems that must be regularly sterilized. They are sterilized by forcing highly compressed hot steam, etc. through the line. Hoses that are resilient enough to forward the materials effectively, however, do not resist heat and pressure very well.

Hose pumps are accordingly removed from the system prior to sterilization and sterilized separately. This approach not only requires extra work but also entails the risk of recontamination when the pump is replaced in the system.

SUMMARY OF THE INVENTION

The object of the present invention is accordingly a method whereby the pump can be sterilized along with the system without damaging the hose.

This object is attained in accordance with the invention in that, before the system is sterilized, the hose is transferred from the pump, but not disconnected from the system's lines, to a device that surrounds it snugly.

The device supports the hose from outside and renders it resistant to the heat and pressure of sterilization. The pump must be designed to allow the hose to be removed from it without being taken off line.

The device employed to carry out the method in accordance with the invention is characterized by comprising two halves, each with a depression shaped and dimensioned to match half the outer surface of the hose and accordingly surrounding it tightly over its total length when the two halves are together.

The depression in one preferred embodiment of the invention is straight. Such a device is particularly simple to manufacture. It does require of course that the line also extend straight through the system, which requires flexible connectors between the hose and the line.

The contour of the depression in another advantageous embodiment is the same as that of the hose when the hose is in the pump. It is particularly easy to transfer the hose from the pump to this embodiment, and the flexible connectors between the hose and the line can be very short or can even be eliminated.

Further advantageous embodiments of the invention are described hereinafter.

Various embodiments of the invention will now be specified with reference to the drawings, wherein

DETAILED DESCRIPTION OF THE INVENTION

Figure 1:
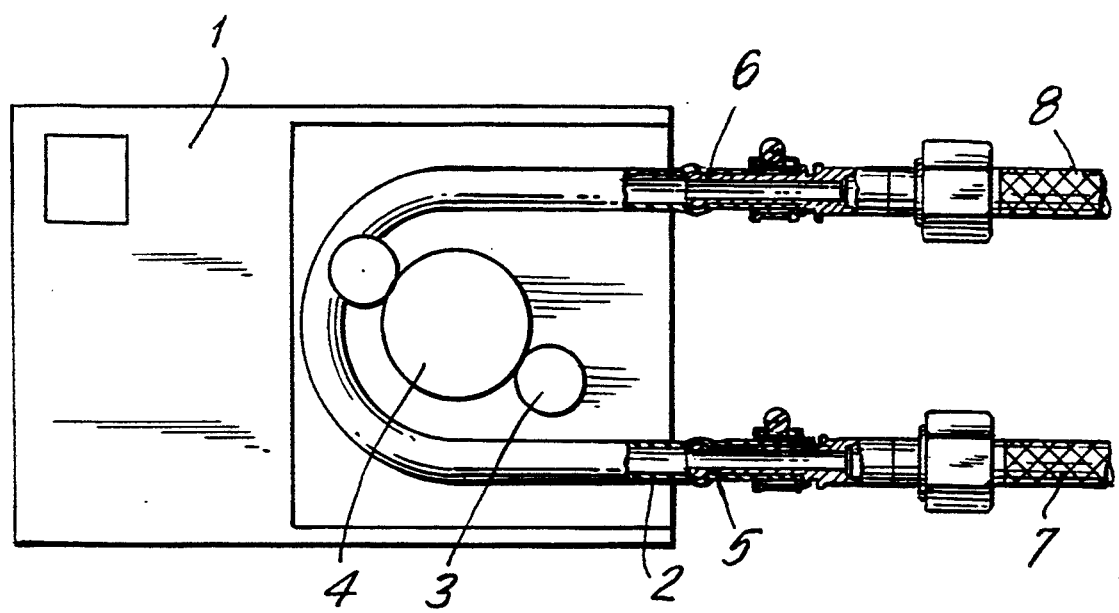
FIG. 1 illustrates a pump with its hose in place.

The hose pump 1 illustrated in FIG. 1 accommodates a hose 2. Material is forced through the hose by rollers 3 that revolve on the circumference of a wheel 4 and squeeze the hose 2. At each end of hose 2 is a connector 5 and 6. Connectors 5 and 6 connect the hose to flexible lines 7 and 8 in an unillustrated material-forwarding system.

Figure 2:
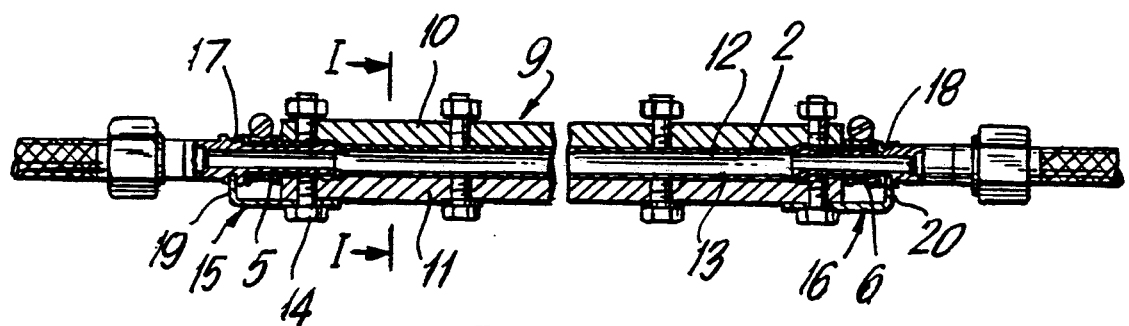
FIG. 2 illustrates a device in accordance with the invention with a straight depression.

Hose 2 is transferred from pump 1 to the device 9 illustrated in FIG. 2 before the system is sterilized. Device 9 is in two halves 10 and 11. Halves 10 and 11 accommodate straight depressions 12 and 13. The halves are secured together by screws 14. Mounted on device 9 are means 15 and 16 that prevent hose 2 from stretching longitudinally during sterilization. Means 15 and 16 comprise grooves 17 and 18 around connectors 5 and 6 that accommodate stops 19, 20 mounted on half 11.

Figure 3:
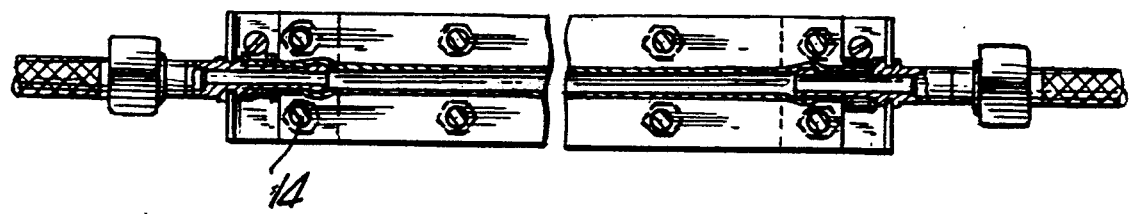
FIG. 3 is a top view of the device in FIG. 2.
Figure 4:
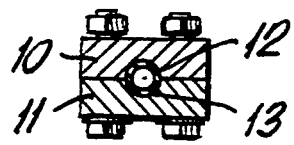
FIG. 4 is a section along the line I—I in FIG. 2.

FIGS. 3 and 4 illustrate the positions of screws 14, the shape of halves 10 and 11, and the contour of depressions 12 and 13.

Figure 5:
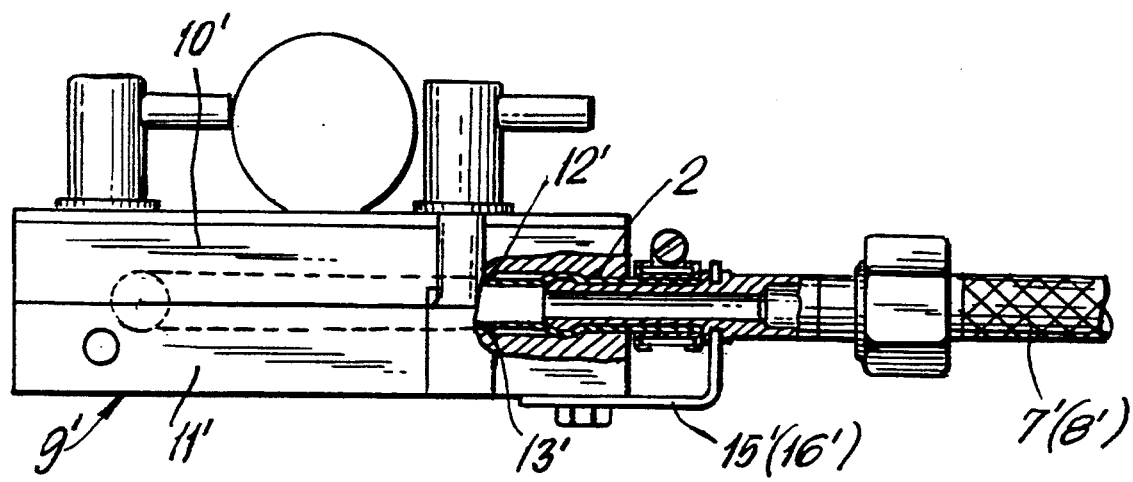
FIG. 5 illustrates a device with a depression that has a U-shaped contour.
Figure 6:
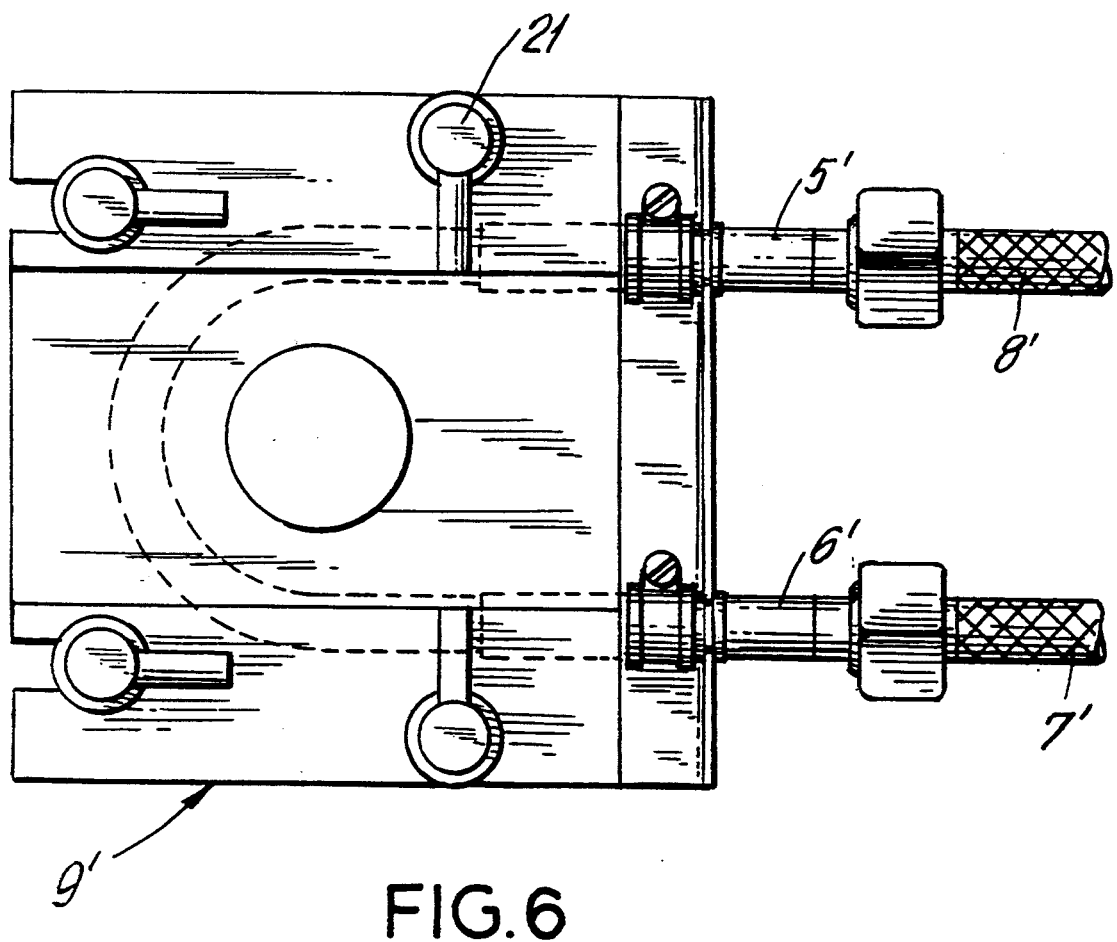
FIG. 6 is a top view of the device illustrated in FIG. 5.

The contour of the depressions 12' and 13' in the embodiment illustrated in FIGS. 5 and 6 matches that of the hose 2 when the hose 2 is in the pump 1 as illustrated in FIG. 1. In this event lines 7' and 8' can be very short and may even be unnecessary. Halves 10' and 11' are held together by rapid releases 21. Hose 2 can be transferred from pump 1 to this embodiment of device 9' especially quickly.

Hose 2 is transferred from pump 1 to device 9' before the system is to be sterilized, and halves 10' and 11' are secured together by screws or rapid releases 21. Connectors 5' and 6' are left in place between hose 2 and system lines 7' and 8'. Device 9' surrounds and supports hose 2 during sterilization, protecting it from radial distortion by pressure and heat. Hose 2 is prevented from stretching longitudinally by means 15' and 16'.

What is claimed is:

1. A method of sterilizing a hose pump hose, comprising the steps of: providing a hose pump having a hose which is removable therefrom; connecting the hose to lines of a system operating in sterile conditions; removing the hose from the hose pump without disconnecting same from the system lines; disposing the removed hose in a sterilizing device which surrounds the hose snugly for protection from heat and pressure; and sterilizing the hose while in the sterilizing device and connected to the system by forcing a heated, pressurized sterilization fluid therethrough.

2. The method of sterilizing a hose pump hose while connected in a system operating in sterile conditions, as in claim 1, wherein the sterilizing device comprises: a body receptive of the hose while connected in the system and comprising two halves each having means forming a depression therein configured to match an outer surface of the hose to surround tightly along the entire length thereof when the two halves are connected and means for releasably connecting the two halves together around the hose while connected in the system for protection of the hose from heat and pressure of sterilization fluid.

3. The method as in claim 2, wherein the depression is straight.

4. The method as in claim 2, wherein the depression has a contour identical with that of the hose when the hose is in the hose pump.

5. The method as in claim 2, wherein the two halves are plastic.

6. The method as in claim 2, wherein means connecting the two halves comprise screws.

7. The method as in claim 2, wherein the means connecting the two halves comprise means for rapidly releasing the two halves from connection.

8. The method as in claim 2, further comprising means for preventing the hose from stretching longitudinally during sterilization.

9. The method as in claim 8, wherein the means for preventing stretching comprises stops mounted on one of the halves and coactive with grooves on connectors connecting the hose to the system.

* * * * *